United States Patent [19]

Lurie

[11] Patent Number: 6,075,005
[45] Date of Patent: Jun. 13, 2000

[54] MEDICAMENTS COMPRISING RELAXIN AND THEIR USE

[76] Inventor: Raziel Lurie, 33 Mota Gur St., Tel Aviv, Israel, 69694

[21] Appl. No.: 09/348,062

[22] Filed: Jul. 6, 1999

[51] Int. Cl.[7] .......................... A61K 38/00; A61K 31/506; A61K 31/44
[52] U.S. Cl. ................. 514/2; 514/275; 514/284
[58] Field of Search ................... 514/2, 284, 275

[56] References Cited

U.S. PATENT DOCUMENTS

| | | | |
|---|---|---|---|
| 3,096,246 | 7/1963 | Doczi ....................................... | 167/74 |
| 4,760,071 | 7/1988 | Rasmusson et al. ..................... | 514/284 |
| 5,023,321 | 6/1991 | Hudson et al. ......................... | 530/324 |

*Primary Examiner*—Raymond Henley, III
*Attorney, Agent, or Firm*—Christopher E. Blank; Lynne M. Blank

[57] ABSTRACT

The present invention relates to a hair growth compositions which contain relaxin or a relaxin analog and an anti-androgenic agent such as finasteride, SKL-105657, estrogen, cyproterone acetate, spironolactor, flutamide, minoxidil or RU58841 as well as to methods for treating androgenic alopecia using such compositions.

15 Claims, No Drawings

MEDICAMENTS COMPRISING RELAXIN AND THEIR USE

BACKGROUND OF THE INVENTION

In humans, each hair follicle goes through repeated cyclical periods of growth including an active growth stage (anagen), which can persist for approximately 2 to 6 years; a transition phase (catagen), which lasts for only a week or two; and a resting period (telogen), which lasts 3 to 4 months. The hair is shed at the end of the telogen phase, and a new hair is grown as the cycle repeats. In the human scalp, which contains approximately 100,000 hair follicles, normally about 86% are in anagen, 1% are in catagen and 13% are in telogen. Therefore, in a normal human adult, approximately 100 hairs are shed from the scalp per day.

Excessive hair loss, or alopecia, may be classified as being one of two types, non-scarring alopecia and scarring alopecia, and can be caused by a wide variety of factors. For example, non-scarring alopecia has been attributed to genetics and advanced age; administration of drugs such as anti-cancer chemotherapeutic drugs and contraceptives; topical use of chemical treatments, such as hair dyes, permanent wave solutions, and straighteners; diseases, such as leprosy or syphilis; illness; allergy; and hair follicle infection. Scarring alopecia may be a consequence of burns (accidental or post surgical from cryosurgery or laser surgery) or trauma, which often causes destruction of follicles.

The most common type of human hair loss is androgenetic alopecia (also known as androgenic alopecia), which is a non-scarring hair loss of telogen hairs caused by an excessive androgen effect in genetically susceptible men and women. Androgens trigger the miniaturization or atrophy of terminal follicles that normally produce thick scalp hair and transforms them into vellus-like follicles, eventually yielding fine, downy hair that is barely perceptible. Androgenetic alopecia is expressed in males as baldness of the vertex of the scalp and is commonly referred to as male pattern baldness. In females, androgenetic alopecia appears as diffuse hair loss or thinning of the frontoparietal areas. As alopecia progresses with age, hairs in these predisposed areas miniaturize and appear to change from terminal hairs to resemble vellus hairs. In addition, as androgenetic alopecia continues, the number of hairs in the active growth anagen phase decreases while there is an increase the number of hairs in the telogen phase.

Androgenetic alopecia, which is sometimes referred to as "common baldness" or "male pattern baldness," independent of its causes, is the cutaneous aping of a particular zone (i.e., the scalp). Androgenetic alopecia can be defined, on one hand, as atrophy, sclerosis or minaturization of the hair follicles. On the other hand, androgenetic alopecia can be defined as a progressive shortening of the average duration of the anagen stage, which results in vellus hair prior to complete disappearance.

Hair loss is an extremely common condition among healthy adult males, and also occurs frequently in adult females. In fact, some degree of alopecia on the vertex from puberty onwards is thought to be a universal phenomenon in both men and women (R. P. R. Dawber (1987) Dermatologica 175:23–28). Alopecia is also frequently observed in both pre- and post-pubertal patients as a side effect of anti-cancer chemotherapy, (A. M. Hussein, et al. (1990) Science 249:1564–1566, B. W. Cline, (1984) Cancer Nursing 7:221–228; A. F. Hood (1986) Med. Clin. North Am. 70:187–209).

Despite the widespread occurrence of androgenetic alopecia, the need for prevention and therapy still exists. The lack of a proven and effective treatment for androgenetic alopecia has caused many afflicted individuals to adopt the practice of wearing a wig or toupee. Another extreme measure used to combat androgenetic alopecia, hair transplant surgery, is not available as an option in many cases (i.e., following chemotherapy) and offers, at best, only a partial remedy. At the same, the latter treatment suffers from a number of disadvantages, including the need for surgery.

A common non-surgical treatment for stimulating hair growth is minoxidil (The Upjohn Company, Kalamazoo, Mich.). A solution of minoxidil as active ingredient is known as Rogaine.RTM. As stated in the Rogaine.RTM. Patient Information Booklet (The Upjohn Company, Kalamazoo, Mich., revised June, 1992) minoxidil is a vasodilatory drug which has serious side effects when administered orally for the treatment of hypertension. At the same time, topical application of minoxidil for the treatment of androgenetic alopecia is only partially effective and suffers from a number of disadvantages. For example, minoxidil is only recommended for treatment of male pattern alopecia of the vertex (i.e., frontal recession), has to be applied twice daily for at least four months, and requires a normal scalp with no local abrasions, dermatitis or sunburn—conditions that can increase absorption into the blood stream and the concomitant risk of side effects. Further, minoxidil is of limited effectiveness. For example, there is no significant increase in terminal hair regrowth between minoxidil and placebo treatment groups after four months of treatment (refer to the Rogaine.RTM. Patient Information Booklet, The Upjohn Company, Kalamazoo, Mich., revised June, 1992). In patients who do respond to minoxidil treatment, the new hair is likely to be shed within a few months after stopping treatment.

Androgens are responsible for many physiological functions in both males and females. Androgen action is mediated by specific intracellular hormone receptors expressed in androgen responsive cells. Testosterone, the major circulating androgen, is secreted by Leydig cells of the testes under the stimulation of pituitary-derived luteinizing hormone (LH). However, reduction of the 4, 5 double bond of testosterone to dihydrotestosterone (DHT) is required in some target tissues, such as prostate and skin, for androgen action. Steroid 5.alpha.-reductases in target tissues catalyze conversion of testosterone to DHT.

The requirement for DHT to act as an agonist in these target tissues has been highlighted by studies of steroid 5.alpha.-reductase deficient individuals who have vestigial prostate glands and do not suffer from male pattern baldness (see McGinley. J. et al., The New England J. of Medicine, 300, 1233 (1979)). Thus, inhibition of the conversion of testosterone to DHT in these target tissues is anticipated to be useful in the treatment of a variety of androgen responsive diseases (i.e., benign prostatic hyperplasia, prostate cancer, acne, male pattern baldness and hirsutism).

Additionally, it has been discovered that two isozymes of 5.alpha.-reductase exist in humans which differ in their tissue distribution, affinity for testosterone, pH profile and sensitivity to inhibitors (see Russell, D. W. et al., J. Clin. Invest., 89, 293 (1992); Russell, D. W. et al., Nature, 354, 159 (1991)). The steroid 5.alpha.-reductase deficient individuals studied by Imperato-McGinley are deficient in the type 2,5.alpha.-reductase enzyme (Russell, D. W. et al., J. Clin. Invest., 90, 799 (1992); Russell, D. W. et al., New England J. Med., 327, 1216 (1992)), which is the predominant isozyme present in the prostate, while the type 1 isozyme is predominant in the skin. The relative value of isozyme specific and dual inhibitors of the two isozymes of 5.alpha.-reductase will depend upon the type of disease treated (benign prostatic hyperplasia, prostate cancer, acne, male pattern baldness or hirsutism) as well as the stage of the disease (prevention versus treatment) and the anticipated side-effects in the intended patients (for example treatment of acne vulgaris in pubescent males).

Because of their valuable therapeutic potential, testosterone 5 alpha reductase inhibitors have been the subject of active research worldwide. For example, see: Hsia, S. and Voight, W., J. Invest. Derm., 62, 224 (1973); Robaire, B. et al., J. Steroid Biochem., 8, 307 (1977); Petrow, V. et al., Steroids, 38, 121 (1981); Liang, T. et al. J. Steroid Biochem., 19, 385 (1983); Holt, D. et al., J. Med. Chem., 33, 937 (1990): U.S. Pat. No. 4,377,584, U.S. Pat. No. 4,760,071 and U.S. Pat. No. 5,017,568. Several particularly promising 5.alpha.-reductase inhibitors are: (1) MK-906 (Merck), known by the generic name, finasteride, and marketed under the trademark, Proscar; (2) SKF-105657 (SmithKline Beecham); and (3) cyproterone acetate.

Finasteride (17.beta.-(N-tert-butylcarbamoyl )-4-aza-5.alpha.-androst-1-ene-3-one), which is marketed by Merck & Co., Inc. under the tradename PROSCAR.RTM., is an inhibitor of 5.alpha.-reductase 2 and is known to be useful for the treatment of hyperandrogenetic conditions. See e.g., U.S. Pat. No. 4,760,071. Finasteride is currently marketed in the United States and worldwide for the treatment of benign prostatic hyperplasia. Finasteride's utility in the treatment of androgenetic alopecia is also disclosed in the following documents: EP 0 285,382, published Oct. 5, 1988; EP 0 285 383, published Oct. 5, 1988; Canadian Patent no. 1,302,277; and Canadian Patent no. 1,302,276.

Androgens are the most obvious regulators of human hair growth in both sexes. Androgens have pradoxically contrasting effects on follicles depending on their location in the body. Androgens stimulate hair growth in many locations (i.e., beard, axilla) while inhibiting scalp hair growth in genetically predisposed individuals. Androgens act on the hair follicles via the dermal papilla, presumably by altering the production of regulatory factors effecting the dermal papilla cells. Cultured dermal papilla cells secrete soluble, proteinaceous factors which are mitogenic for other dermal papilla cells, outer root sheath cells, epidermal keratinocytes and endothelial cells. Androgen sensitive cells from beard or balding scalp reflect their in vivo androgenetic responses by responding to testosterone, by increasing (i.e., beard) or decreasing (i.e., balding) their mitogenic ability.

The dermal papilla is a connective tissue structure situated at the base of hair follicles. The dermal papilla is composed of specialized fibroblast cells which demonstrate major changes in terms of cell morphology, vascularization, composition and volume of extracellular matrix. During anagen the dermal papilla cells show intracellular structures indicating on going protein synthesis and there is an active vascularization process, whereas during the telogen it is quiescent and non vascularized.

The dermal papilla extracellular matrix contains collagen laminin fibronectin and haparin sulfate proteoglycan. During the transition form anagen to catagen the extracellular matrix diminishes in volume and in the telgoen phase it is almost nonexistent. Also in the telogen phase fibronectin, laminin and proteoglicans diminwhile the collagen content is increased in the interfollicular dermis and in the dermal papilla. There is some evidence indicating proteoglicans involvement in the hair growth process in addition to the above mentioned changed pattern of expression during the hair growth cycle. Injection of glycosamonoglycans in to skin of rabbits stimulated hair growth. The accumulation of proteoglycans in the skin, like in pretibial myxedema is associated with hypertrichosis.

The present invention relates to the use of Relaxin, in the manufacture of medicaments having a novel application, to a method of use in which relaxin is utilized for the treatment and prevention of certain conditions and to pharmaceutical compositions comprising relaxin. Relaxin otherwise known as Cervilaxin, and formerly referred to as Releasin, is a polypeptide hormone secreted by the corpora lutea of many mamalian species during pregnancy.

As described in U.S. Pat. No. 3,096,246, the contents of which are incorporated herein by reference, relaxin is present in the ovaries of animals and may be extracted therefrom. It is believed to be a hormone of pregancy and has aroused great interest in the field of medical research. For example, it has been known to cause uterine cervix relaxation in cows; to increase the dilatability of uterine cervix in ovariectomized estrogen-primed hogs; to cause definite milk let-down in sheep, and, to a lesser extent, in cows, and to cause marked lobulo-alveolar growth of the mammary gland in rats; and, in the clinic, it has been found to cause dilation of the uterine cervix in near-term pregnant women who fail to dilate after injections of pitocin, and to stop premature labor in certain female patients, allow them to go through to term.

EP 08664g, the contents of which are incorporated he rein by reference, relates to the molecular cloning and characterization of the gene sequence coding for porcine relaxin. Thus, recombinant DNA techniques for the preparation of procine relaxin were described more than ten years ago. However, before the advent of the present invention, application of relaxin has been restricted essentially to pregnancy- and gynecologically-related uses.

SUMMARY OF THE INVENTION

It has now been found in accordance with the present invention that relaxin and relaxin analog compounds in combination with anti-androgenic agents (i.e., relaxin plus finasteride, SKL-105657, estrogen, Cyproterone acetate, spironolactor, Flutamide, topical minoxidil 2%, topical minoxidil 5%, or RU58841.) can be used to treat and prevent androgenetic alopecia and related conditions, and thus to encourage hair growth and to prevent hair loss. Furthermore, it has been found that that relaxin and relaxin analog compounds in combination with estrogenic hormones prevents hair loss in females.

The term "relaxin" means human relaxin, including full length relaxin or a portion of the relaxin molecule that retains biological activity [as described in U.S. Pat. No. 5,023,321, preferably recombinant human relaxin (H2)] and other active agents with relaxin-like activity, such as agents that competitively displace bound relaxin from a receptor. Relaxin can be made by any method known to those skilled in the art, preferably as described in U.S. Pat. No. 4,835,251 or U.S. Pat. No. 5,811,395 issued to Schwabe. The term "relaxin analog," unless stated otherwise, refers to the Asb(B14) analog and derivatives thereof, including full length Asp(B14) relaxin or a portion of the Asp(B14) relaxin molecule that retains biological activity [as described in U.S. Pat. No. 5,023,321, preferably recombinant human relaxin (H2)] and other active agents with relaxin-like activity, such as agents that competitively displace bound relax in from a receptor.

In one aspect, the invention provides use of relaxin and relaxin analog compounds in combination with anti-androgenetic agents in the manufacture of a medicament for the treatment and prevention of androgenetic alopecia and related conditions (such as atrophy, sclerosis and miniaturization of the hair and hair follicles). The medicament may comprise the relaxin or relaxin analog compounds/ anitandrogenetic agent combination in a pharmaceutically acceptable (i.e., topically acceptable) carrier, and may be used, for example, for prolonging the duration of the anagen stage of hair growth.

In another aspect of the invention, the invention provides a method for the treatment and prevention of androgenetic alopecia and related conditions, which comprises administering to a human in which said treatment or prevention is desired, an effective amount of relaxin or relaxin compounds. In this method, relaxin or relaxin compounds may be administered in combination with a pharmaceutically acceptable (i.e., a topically acceptable) carrier. The method may thus be used, for example, for the treatment and prevention of a condition selected from atrophy, sclerosis and miniaturization of the hair and hair follicles, or for proloning the duration of the anagen stage of hair growth.

DETAILED DESCRIPTION OF THE INVENTION

As is known in the art, cyclic activity of the hair is divided into three stages: a period of active growth known as anagen, a short transition phase called catagen, and a resting period which ends in hair loss, called telogen.

It is also an accepted fact that the percentage of follicles in anagen rises steeply during pregnancy, when as many as ninety-five percent (95%) of the follicles are active. Two to four months after parturition, the proportion falls to less than seventy percent (70%). Therefore, it appears that the hormonal conditions of late pregnancy prolong anagen, and follicles are consequently precipitated into telogen via catagen after parturition.

In hair follicles there are two important enzymes which have a key role in androgen metabolis; these are (1) 5 alpha reductase, and (2) aromatase. The object of the present invention is to decrease the activity of 5 alpha reductase and increase the activity of aromatase.

The clearest example of systematic influence on the human hair growth cycle is pregnancy. During pregnancy there is a marked increase in the proportion of follicles in the anagen phase. After termination of the pregnancy, whether by birth or otherwise, large numbers of follicles enter telogen, thereby causing shedding (i.e., postpartum telogen effluvium). These changes are related to the hormonal changes during pregnancy. One of the specific problems of women with androgenetic alopecia is polycystic ovary disease, in which there is an inadequate function or absence of the corpus luteum. It is the corpus luteum that is the main source of relaxin.

5 alpha reductase converts testosterone to dihydrotestosterone. The presence of dihydrotestosterone must be limited, in so far as possible. Limiting dihydrotestosterone is accomplished by inhibiting the activity of 5 alpha reductase.

Increased activity of aromatase will convert testosterone to estrogens, such as estrone and estradiol, which is desirable. Aromatase is located specifically in the outer root sheath in active follicles in quantities 2–5 times higher in women than in men.

Cytokines are small proteins involved in cell to cell communication. They include peptide growth factors (i.e., EGF, IGF-1, FGF's, NGF) and interlukins (i.e., IL1, IL2, TNF's). They have an important role in cell growth regulation and differentiation of many cell types, including skin fibroblast and keratinocytes. They act through specific cell surface receptors and they have fast, potent and local action. There are over 50 or more known complex biological control systems.

Cytokines act as (1) inhibitors of hair growth in vitro (i.e., TGF-BETA, IL1 -ALPHA, IL1-BETA, TNF-ALPHA) and (2) modulators of catagen (i.e., KGF, FGF).

There is no single hair growth factor. Hair growth is an interaction between several different cytokines, however, two cytokines stand out from the rest in terms of importance; these are IGF-1 and TGF-BETA. IGF-1 maintains hair follicles in the anagen phase. The follicles enter catagen if IGF-1 is absent. IGF-1 and IGF-1-R gene expression declines. TGF-BETA triggers the catagen phase. It is a potent inhibitor of hair growth in vitro. Relaxin increases IGF-1 and decreases TGF-BETA therefore it has the desired effect on hair growth and prevention of hair loss.

It is also known that localized hypertrichosis is associated with an increase in the cutaneous blood flow and the increase of perfusion caused by vasodilator may contribute to hair growth: relaxin influences vasodialation through its influence to increase the nitric oxide level and its activity in increasing VGF-1 and VGF.

From relevant histology we learn that those afflicted with androgenetic alopecia demonstrate: (1) an increase of 5 alpha reductase activity: (2) an increase in the production of dihydrotestosterone; (3) lower aromatase activity: and (4) reduced production of estradiol. Those afflicted with androgenetic alopecia also demonstrate inflammation, follicular streamers, dermal and perifollicular fibrosis, atrophy and sclerosis with net results of miniturization of the hair follicle. Moreover, androgenetic alopecia is characterized by a progressive shortening of the average duration of the anagen phase with net results of terminal hair transformation into vellus hair before complete disappearance.

In order to prevent androgenetic alopecia one must look for a substance that: (1) will have anti androgenetic effect, such as cyproterone acetate, spironolactor, Flutamide, all of which are useful for females, and topical minoxidil 2% and 5%, and all blockers of androgenetic receptors, such as RU58841 and blocker of 5 alpha reductase such as Finasteride (only for treatement of males), which are useful for both males and females; (2) will prolong the duration of the anagen phase and prevent the transfer to the catagen phase; (3) control the production and the non-production of cytokines; (4) cause remodelling of the collagen matrix and increase the concentration of various extracellular components (i.e., proteoglicans and fibronectin laminin); and (5) will have a vasodilatory effect on capillary loops of the dermal papilla, such as nitric oxide, which is increased in the presence of Relaxin.

Relaxin is a small polypeptide member of the protein hormone family, which also includes insulin and insulin like growth factors IGF-1 and IGF-2. Relaxin is expressed during pregnancy and research demonstrates that relaxin: (1) exerts a stimulatory synergistic effect on aromatase activity (anti-androgenetic effect) in human endometrial stromal cells: (2) promotes growth of procine granulosa cells by stimulation of IGF-1; (3) is a potent collagen down regulatory agent which interrupts collagen expression pretransitionally and at a point in the collagen induction pathway common to both TGF-BETA and IL1-BETA (two stimulatros of collagen expression; (4) influences molecules of the extracellular matrix of connective tissue increasing the content of proteoglycans in rat uterus and cervix; (5) promotes synthesis of laminin in endothermal stromal cells in mice; (6) assists in the partial degradation of the fetal membrane extracellular matrix and causes activation of an enzyme cascade resulting in remodeling and changes in the structure of this complex matrix; (7) exerts a vasodilator effect through stimulation of nitric oxide production in its target cells; (8) blocks absorption of calcium by cytoplasmic membranes of the smooth muscle cells of blood vessel walls; (9) binds with specificity to the skin, particularly to the stratum granulosum and the malpighian layer (i.e., strata spinosum and germinativum) of the epidermis and the outer root of the hair follicles of pregnant pigs; and (10) prolongs the duration of the anagen phase and prevents the transfer to the catagen phase.

The patterns of relaxin and relaxin binding cells indicates that in the hair follicles these patterns may act not only directly as mitogen on the germinative cells and on the outer root sheath, but also indirectly on the dermal papilla stimulating the production of growth factors. The binding cells of relaxin in the outer root sheath indicate that relaxin may play a role in regulating terminal differentiation.

Relaxin influences the fibroblasts and fibroblast-like cells of the pilosebacious unit. Relaxin treatment, either topically or systemically, will result in preventing atrophy, sclerosis and minaturization of the hair, by prolonging the duration of the anagen stage, or otherwise. It will remodulate the cutaneous aging process in general and in particular it will remodulate androgenetic alopecia in both males and females.

According to the present invention, there is provided a composition which can be applied topically in the form of lotion, ointment, gel or cream, or systemically for internal or parenteral use, in the form of capsules, tablets or ampules, for treatement of androgenetic alopecia and related conditions such as alopecia areata, anagen effluvium, telogen effuvium and post-partum telogen alopecia, diffuse alopecia, and alopecia androgenetica.

Said compositions can be in the form of creams, lotions, ointments, gels or creams, prepared for use in any conventional manner, in admixture with one or more physiologically acceptable carriers and diluents.

The compositions may take such forms as suspension, solutions, or emulsions in oily or aqueous vehicles, and may contain agents such as emulsifying, suspending, stabilizing, gelling and/or dispersing agents. Alternatively, the active ingredients may be in powder form for constitution with a suitable vehicle (i.e., sterile, pyrogen-free water) before use and may compounded into tablet, powder or capsule form using techniques well known to those skilled in the formulary art.

While it is possible for the active ingredient cobination to be administered alone, it is preferable to present them as pharmaceutical formulations. The formulations of the present invention comprise at least one active ingredient, as above defined, together with one or more acceptable carriers therefor and optionally other therapeutic ingredients. The carrier(s) must be acceptable in the sense of being compatible with the other ingredients of the formulation and not deleterious to the recipient thereof.

The formulations may conveniently be presented in unit dosage form and may be prepared by any of the methods well known in the art of pharmacy. Such methods include the step of bringing into association the active ingredient with the carrier, which constitutes one or more accessory ingredients. In general, the formulations are prepared by uniformly and intimately bringing into association the active ingredient with liquid carriers or finely divided solid carriers, or both, and then, if necessary, shaping the product.

The formulations are preferably applied as a topical lotion, ointment, gel or cream, containing the active ingredient in a concentration of, for example, 0.005 to 10.0 percent, preferably 0.01 to 5.0 percent w/w and most preferably 0.05 to 2.0 percent w/w. When formulated in cream, the active ingredients may be employed with an oil-in-water cream base.

If desired, the aqueous phase of the cream base may include, for example, at least thirty percent (30%) w/w of a polyhydric alcohol (i.e., an alcohol having two or more hydroxyl groups such as propylene glycol, butane-1,3-diol, mannitol, sorbitol, glycerol and polyethylene glycol and mixtures thereof. The topical formulations many desirably include a compound which enhances absorption or penetration of the active ingredient through the skin or other affected areas. Examples of such dermal penetration enhancers include dimethylsulphoxide and related analogues.

The oily phase of the emulsions of this invention may be constituted from known ingredients in a known manner. The oil phase may comprise merely an emulsifier it desirably comprises a mixture of at least one emulsifier with a fat or an oil or with both a fat and an oil. Preferably, a hydrophilic emulsifier is included together with a lipophilic emulsifier, which acts as a stabilizer. It is also preferred to include both an oil and a fat. Together, the emulsifier(s), with or without stabilizers(s), make up the so-called emulsifying wax, and the wax, together with the oil and/or fat, make up the so-called emulsifying ointment base, which forms the oily dispersed phase of the cream formulations.

Emulgents and emulsion stabilizers suitable for use in the formulation of the present invention include Tween 60, Span 80, cetostearyl alcohol, myristyl alcohol, glycerl monostearate and sodium lauryl sulphate.

The choice of suitable oils or fats for the formulation is based on achieving the desired cosmetic properties, because the solubility of the active compound in most oils likely to be used in pharmaceutical emulsion formulations is very low. Therefore, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester or coconut fatty acids, isopropyl myristate, decyl oleate, isopropyl palmitate, butyl stearate, 2-ethylhexyl palmitat, or a blend of branched chain esters known as Crodamol CAP may be used, the last three being preferred esters. These may be used alone or in combination, depending on the properties required. Alternatively, high melting-point lipids, such as white soft paraffin and/or liquid paraffin, or other mineral oils, can be used.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples, which include preferred embodiments, will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLE 1

Lotion

| | |
|---|---|
| Relaxin | 100 mg |
| cyproterone acetate | 100 mg |
| Deionized water | 850 ml |
| Ethanol | 150 ml |

The Relaxin and anti-adnogenetic agent were dissolved in the mixture of solvents.

EXAMPLE 2

Gel

| | |
|---|---|
| Relaxin | 20 mg |
| Flutamide | 10 mg |
| Deionized water | 49.0 g |
| Ethanol | 49.0 g |
| Carbomer 934 P | 0.5 g |
| Triethanolamine | 0.5 g |

The Relaxin was dissolved in the water/alcohol mixture. The carbomer was dispersed in the solution and the triethanolamine was added while agitating constantly.

EXAMPLE 3

Gel

| | |
|---|---|
| Relaxin | 5.0 mg |
| Spironolactor | 5.0 mg |
| Deionized water | 83.9 g |
| Ethanol | 75.0 g |
| Carbomer 934 P | 0.25 g |
| HPMC 4000 cps | 0.60 g |
| Triethanolamine | 0.25 g |

The Relaxin and HPMC were dissolved in the water and the alcohol was added. The carbomer was dispersed in the solution and triethanolamine was added while agitating.

EXAMPLE 3a

Gel

| | |
|---|---|
| Relaxin | 5.0 mg |
| Minoxidil | 1.0 mg |
| Deionized water | 83.9 g |
| Ethanol | 75.0 g |
| Carbomer 934 P | 0.25 g |
| HPMC 4000 cps | 0.60 g |
| Triethanolamine | 0.25 g |

The Relaxin and minoxidil and HPMC were dissolved in the water and the alcohol was added. The carbomer was dispersed in the solution and triethanolamine was added while agitating.

EXAMPLE 3b

Gel

| | |
|---|---|
| Relaxin | 5.0 mg |
| Dihydrotestosterone | 3.0 mg |
| Deionized water | 83.9 g |
| Ethanol | 75.0 g |
| Carbomer 934 P | 0.25 g |
| HPMC 4000 cps | 0.60 g |
| Triethanolamine | 0.25 g |

The active ingredients were dissolved in the water and the alcohol was added. The carbomer was dispersed in the solution and triethanolamine was added while agitating.

EXAMPLE 4

Cream

| | |
|---|---|
| Relaxin | 1.0 g |
| Estrogen | 200 mg |
| Cetylester wax | 2.0 g |
| Polysorbate 60 | 1.0 g |
| Paraffin oil | 10.0 g |
| Carbomer 934 P | 1.0 g |
| Glycerol | 5.0 g |
| Potassium sorbate | 0.2 g |
| Ammonia 25% | 0.7 g |
| Deionized water | to 100 g |

The Relaxin, potassium sorbate, and glycerol were dissolved in water and the carbomer was dispersed in the solution, at room temperature. The cetylester wax, polysorbate and paraffin oil were heated to dissolve, and were mixed with the aqueous portion at room temperature. Ammonia was added to gel the carbomer.

EXAMPLE 5

Tablets

| Quantities per tablet: | |
|---|---|
| Relaxin | 100 mg |
| Minoxidil | 50 mg |
| Lactose | 180 mg |
| Polyvinylpyrrolidone | 10 mg |
| Sodium starch glycollate | 75 mg |
| Magnesium stearate | 125 mg |

The Relaxin and the polyvinylpyrrolidone were dissolved in a quantity of deionized water and the lactose and sodium starch glycollate were granulated in accordance with normal procedure. The granulation was dried and the magnesium stearate added. The mixture was compressed into tablets.

EXAMPLE 6

Capsules

| Quantities per capsule: | |
|---|---|
| Relaxin | 20 mg |
| Minoxidil | 20 mg |
| Microcrystalline cellulose | 100 mg |
| Colloidal silicon dioxide | 3 mg |

The ingredients were thoroughly blended and filled into hard gelatin capsules. Capsules with 25 to 200 mg of dihydrotestosterone in addition to relaxin can be compounded as well.

EXAMPLE 7

Ampoules or Multidose Ampoules

| | |
|---|---|
| Relaxin analog | 50 mg |
| Flutamide | 25 mg |
| Benzyl alcohol | 20 mg |
| Water for injection | to 1 ml |

The ingredients were dissolved in the water for injection and the solution sterilized by filtration. The ampoules were filled and sealed under aseptic conditions.

EXAMPLE 8

Implant

| | |
|---|---|
| Relaxin | 200 mg |
| Progesterone | 150 mg |

In a suitable non-toxic medium (i.e., silicon polymer) to act as an embedding agent.

EXAMPLE 9

Slow Release Patch

This is spread onto a polyester layer with an adhesive such as poly-isobutylene, and covered with a siliconized polyester release liner.

EXAMPLE 10

Shampoo

| | |
|---|---|
| Relaxin analog | 1 g |
| Spironolactor | 0.5 g |
| Sodium lauryl ether suphate | 30 g |
| Diethanolamine of coconut oil fatty acids | 6 g |
| Water | 62 g |

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

Further Examples of Mixtures of Active Components

Below are specific active component mixtures that will be useful in the practice of the invention:

| | |
|---|---|
| Example A1 | |
| Cyproterone acetate | 2 mg |
| Relaxin | 2 mg |
| Ethinylestadiol | 0.035 mg |
| Example A2 | |
| Gestodene | 0.075 mg |
| Relaxin | 2 mg |
| Example A3 | |
| Gestodene | 75 mcg |
| Ethinylestadiol | 20 mcg |
| Relaxin | 1750 mcg |
| Example A4 | |
| Ethinylestadiol | 0.020 mg |
| Desorgestel | 0.150 mg |
| Relaxin | 0.70 mg |
| Example A5 | |
| Finasteride | 1.0 mg |
| Relaxin | 2.0 mg |

What is claimed is:

1. A hair growth pharmaceutical composition comprising:
   relaxin or a relaxin analog, and
   an anti-androgenetic agent selected from the group consisting of, Finasteride, SKL-105657, estrogen, Cyproterone acetate, spironolactor, Flutamide, minoxidil and RU58841.

2. A method for the treatment of androgenetic alopecia comprising:
   providing to a patient an effective amount of said hair growth composition comprising
   relaxin or a relaxin analog, and
   an anti-androgenetic agent selected from the group consisting of, finasteride, SKL-105657, estrogen, Cyproterone acetate, spironolactor, Flutamide, minoxidil and RU58841.

3. The method of claim 2, further comprising administering said hair growth pharmaceutical in combination with a pharmaceutically acceptable carrier.

4. The method of claim 3, further comprising administering said hair growth pharmaceutical in combination with a pharmaceutically acceptable carrier, wherein said pharmaceutically acceptable carrier is a topical carrier.

5. The method of claim 2, further comprising administering said hair growth pharmaceutical in a combination with a pharmaceutically acceptable carrier, wherein said pharmaceutically acceptable carrier is a topically acceptable carrier, and wherein said administering step comprises administering said hair growth pharmaceutical to the scalp of said human, wherein said hair growth pharmaceutical and said topically acceptable carrier are combined into a lotion, ointment, gel or cream containing relaxin in a concentration of 0.001 to 1.0 percent by weight.

6. The method of claim 2, further comprising administering said hair growth pharmaceutical in a combination with a pharmaceutically acceptable carrier, wherein said pharmaceutically acceptable carrier is oral dosage form.

7. The method of claim 2, further comprising administering said hair growth pharmaceutical in a combination with a pharmaceutically acceptable carrier, wherein said pharmaceutically acceptable carrier is a topically acceptable carrier, and wherein said administering step comprises administering said hair growth pharmaceutical to the scalp of said human, wherein said hair growth pharmaceutical and said topically acceptable carrier are combined into a lotion, ointment, gel or cream containing relaxin in a concentration of 0.05 to 0.5 percent by weight.

8. A method for the treatment of androgenetic alopecia comprising:

providing a composition comprising an effective amount of relaxin and an anit-androgenetic agent.

9. The method of claim 8, further comprising administering said hair growth composition in combination with a pharmaceutically acceptable carrier.

10. The method of claim 9, wherein said pharmaceutically acceptable carrier is a topical carrier.

11. The method of claim 9, wherein said pharmaceutically acceptable carrier is an oral dosage form.

12. The method of claim 9 wherein said composition comprising an effective amount of relaxin and an anit-androgenetic agent has a weight concentration of 0.01 to 1.0 percent by weight of active agent.

13. The method of claim 12, wherein said active component is present at between 0.05 and 0.5 percent by weight.

14. A hair growth pharmaceutical composition comprising:

relaxin, and an anti-androgenetic agent selected from the group consisting of, Finasteride, SKL-105657, estrogen, Cyproterone acetate, spironolactor, Flutamide, minoxidil and RU58841.

15. A hair growth pharmaceutical composition comprising:

a relaxin analog, and an anti-androgenetic agent selected from the group consisting of, Finasteride, SKL-105657, estrogen, Cyproterone acetate, spironolactor, Flutamide, minoxidil and RU58841.

* * * * *